(12) United States Patent
Shi et al.

(10) Patent No.: US 10,261,577 B2
(45) Date of Patent: Apr. 16, 2019

(54) METHOD AND DEVICE FOR DETERMINING INPUT INFORMATION

(71) Applicant: BEIJING ZHIGU RUI TUO TECH CO., LTD., Beijing (CN)

(72) Inventors: Yuanchun Shi, Beijing (CN); Yuntao Wang, Beijing (CN); Chun Yu, Beijing (CN); Lin Du, Beijing (CN)

(73) Assignee: Beijing Zhigu Rui Tuo Tech Co., Ltd., Beijing (CN)

( * ) Notice: Subject to any disclaimer, the term of this patent is extended or adjusted under 35 U.S.C. 154(b) by 0 days.

(21) Appl. No.: 15/548,462

(22) PCT Filed: Jan. 7, 2016

(86) PCT No.: PCT/CN2016/070398
§ 371 (c)(1),
(2) Date: Aug. 3, 2017

(87) PCT Pub. No.: WO2016/127744
PCT Pub. Date: Aug. 18, 2016

(65) Prior Publication Data
US 2018/0018015 A1 Jan. 18, 2018

(30) Foreign Application Priority Data
Feb. 10, 2015 (CN) .......................... 2015 1 0069927

(51) Int. Cl.
*G09G 5/00* (2006.01)
*G06F 3/01* (2006.01)
(Continued)

(52) U.S. Cl.
CPC ............ *G06F 3/011* (2013.01); *A61B 5/0261* (2013.01); *A61B 5/6826* (2013.01); *A61B 8/06* (2013.01);
(Continued)

(58) Field of Classification Search
CPC ...... G06F 3/0383; G06F 3/0421; G06F 3/011; G06F 3/017; G06F 1/163; G01P 3/36;
(Continued)

(56) References Cited

U.S. PATENT DOCUMENTS

| 6,707,027 B2 * | 3/2004 | Liess ..................... G01P 3/366 250/221 |
| 7,339,683 B2 * | 3/2008 | Weijers ................. G06F 3/0383 356/519 |

(Continued)

FOREIGN PATENT DOCUMENTS

| CN | 1797294 A | 7/2006 |
| CN | 103049090 A | 4/2013 |

(Continued)

OTHER PUBLICATIONS

First Notice issued by China State Intellectual Property Office, dated Mar. 20, 2017 for Chinese Patent Application No. 201510069927.5 with search report.
(Continued)

*Primary Examiner* — Joe H Cheng
(74) *Attorney, Agent, or Firm* — Sheppard, Mullin, Richter & Hampton LLP

(57) ABSTRACT

The present application provides a method and device for determining input information, and relates to the field of a wearable device. The method comprises in response to a first part of a body of a user executing an action, acquiring target blood-flow information about the first part or a second part that corresponds to the first part; and determining input information according to the target blood-flow information and reference information. According to the method and device, the body of the user is used as an input interface, to cause an interaction area to be increased, which helps to improve input efficiency and user experience.

23 Claims, 11 Drawing Sheets

(51) Int. Cl.
*A61B 8/06* (2006.01)
*G06F 1/16* (2006.01)
*A61B 8/08* (2006.01)
*A61B 5/026* (2006.01)
*A61B 5/00* (2006.01)
*G06K 9/00* (2006.01)

(52) U.S. Cl.
CPC .............. *A61B 8/488* (2013.01); *G06F 1/163* (2013.01); *A61B 8/5223* (2013.01); *A61B 2503/12* (2013.01); *G06F 3/017* (2013.01); *G06K 9/0053* (2013.01); *G06K 9/00355* (2013.01); *G06K 9/00543* (2013.01)

(58) Field of Classification Search
CPC . G01P 3/366; A61B 5/00; A61B 5/026; A61B 5/0261; A61B 5/6826; A61B 8/06; A61B 8/08; A61B 8/488; A61B 8/5223; A61B 2503/12; G06K 9/00355; G06K 9/0053; G06K 9/00543
See application file for complete search history.

(56) References Cited

U.S. PATENT DOCUMENTS

| | | | | |
|---|---|---|---|---|
| 7,589,709 | B2* | 9/2009 | Liess ................... | G06F 3/0421 345/157 |
| 8,217,896 | B2* | 7/2012 | Zeng ................... | G06F 3/03543 345/158 |
| 2005/0156875 | A1 | 7/2005 | Kong | |
| 2007/0164201 | A1 | 7/2007 | Liess et al. | |
| 2008/0208016 | A1* | 8/2008 | Hughes ................ | A61B 5/0533 600/301 |
| 2010/0249619 | A1* | 9/2010 | Kasama ............... | A61B 5/02416 600/502 |
| 2010/0286533 | A1* | 11/2010 | Lee ..................... | A61B 5/0205 600/484 |
| 2010/0331649 | A1* | 12/2010 | Chou .................. | A61B 5/0006 600/364 |
| 2012/0295589 | A1* | 11/2012 | Alexander .......... | H04L 63/0861 455/411 |
| 2013/0154919 | A1 | 6/2013 | Tan et al. | |
| 2014/0323836 | A1* | 10/2014 | Kusukame ........... | A61B 5/6891 600/344 |
| 2015/0026647 | A1* | 1/2015 | Park ..................... | G06F 3/0488 715/863 |
| 2016/0005291 | A1* | 1/2016 | Takahashi ............ | G04G 13/02 340/575 |
| 2016/0058300 | A1* | 3/2016 | Yoon ................... | A61B 5/0059 600/480 |
| 2016/0331324 | A1* | 11/2016 | Choi ................... | A61B 5/6843 |
| 2017/0224235 | A1* | 8/2017 | Sugimoto ............ | A61B 5/0261 |
| 2017/0235366 | A1* | 8/2017 | Liu ...................... | G06F 3/015 345/156 |
| 2017/0258349 | A1* | 9/2017 | Watanabe ............ | A61B 5/0432 |
| 2018/0018016 | A1* | 1/2018 | Shi ...................... | G06F 3/011 |
| 2018/0035903 | A1* | 2/2018 | Shi ...................... | A61B 5/0295 |
| 2018/0049647 | A1* | 2/2018 | Shi ...................... | A61B 5/02 |

FOREIGN PATENT DOCUMENTS

| | | |
|---|---|---|
| CN | 103941874 A | 7/2014 |
| CN | 104049752 A | 9/2014 |
| CN | 104270175 A | 1/2015 |
| CN | 104656895 A | 5/2015 |
| CN | 104656896 A | 5/2015 |
| CN | 104699241 A | 6/2015 |
| CN | 104699242 A | 6/2015 |

OTHER PUBLICATIONS

Second Notice issued by China State Intellectual Property Office, dated Sep. 18, 2017 for Chinese Patent Application No. 201510069927.5.
Notification to Grant Patent Right for Invention issued by China State Intellectual Property Office, dated Dec. 5, 2017 for Chinese Patent Application No. 201510069927.5.
International Search Report and Written Opinion for Application No. PCT/CN2016/070398, dated Apr. 7, 2016, 10 pages.
Morganti, E. et al., "A smart watch with embedded sensors to recognize objects, grasps and forearm gestures," International Symposium on Robotics and Intelligent Sensors, Procedia Engineering, 2012, vol. 41, p. 1169-1175.
Yousefi, R. et al., "Adaptive Cancellation of Motion Artifact in Wearable Biosensors," 34th Annual International Conference of the IEEE EMBS, Sep. 2012, p. 2004-2008.

* cited by examiner

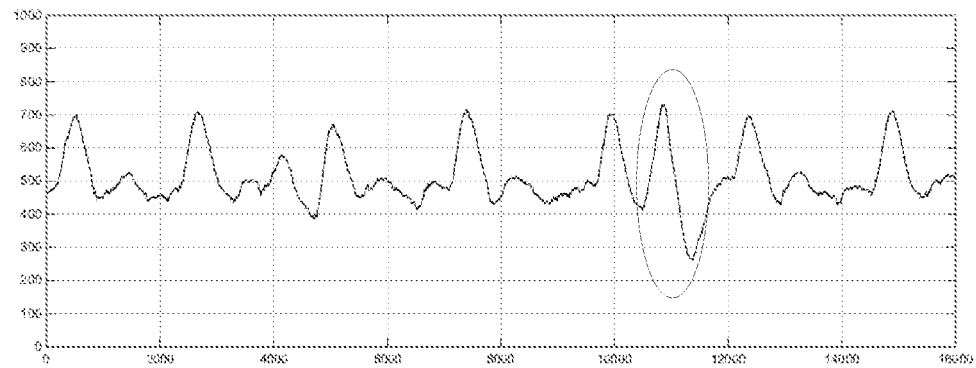
FIG. 10
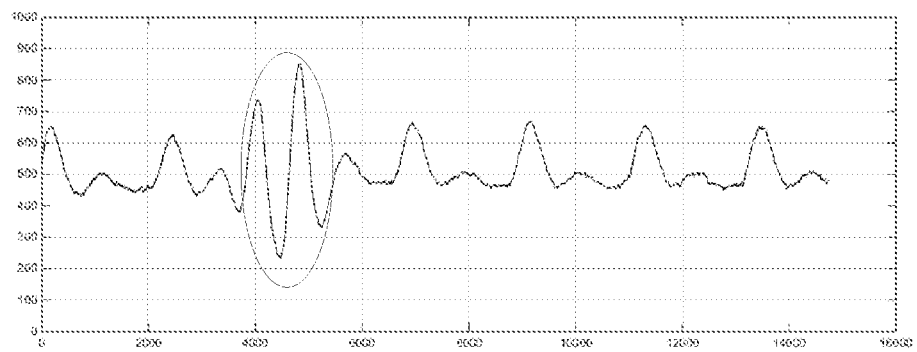
FIG. 11
S14121a
Separately calculate the similarity between a waveform of target difference information and at least one known waveform, and determine a target known waveform according to a calculation result
S14122a
Determine a first part and/or an action according to the target known waveform
FIG. 12

METHOD AND DEVICE FOR DETERMINING INPUT INFORMATION

CROSS-REFERENCE TO RELATED APPLICATIONS

The present application is a National Phase Application of International Application No. PCT/CN2016/070398, filed on Jan. 7, 2016, which claims priority to and benefit of Chinese Patent Application No. 201510069927.5, filed on Feb. 10, 2015, and entitled "Method and Device for Determining Input Information". Both of the above-referenced applications are incorporated into the present application by reference herein in their entirety.

TECHNICAL FIELD

The present application relates to the field of wearable devices, and in particular, to methods and devices for determining input information.

BACKGROUND

With the popularity of electronic devices, people use and control the electronic device to help with work, study, and entertainment almost every day. Enabling a user to conveniently and quickly control an electronic device has been a long-pursed goal of manufacturers of electronic devices.

A wearable device (such as a smart watch, smart gloves, and smart accessories) among electronic devices usually has characteristics such as being attached to users, compact, and low energy consumption. These characteristics result in that most of wearable devices have a small input area and low input capability.

SUMMARY

An objective of the present application is to provide methods and devices for determining input information.

According to an aspect of at least one embodiment of the present application, a method for determining input information is provided. The method comprises:
  in response to a first part of a body of a user executing an action, acquiring target Doppler measurement information about the first part or a second part that corresponds to the first part; and
  determining input information according to the target Doppler measurement information and reference information.

According to another aspect of at least one embodiment of the present application, a device for determining input information is provided. The device comprises:
  an acquiring module, configured to acquire target Doppler measurement information about a first part of a body of a user or a second part that corresponds to the first part, in response to the first part executing an action; and
  a determining module, configured to determine input information according to the target Doppler measurement information and reference information.

According to another aspect of at least one embodiment of the present application, a method for determining input information is provided. The method comprises:
  in response to a first part of a body of a user executing an action, acquiring target blood-flow information about the first part or a second part that corresponds to the first part; and
  determining input information according to the target blood-flow information and reference information.

According to another aspect of at least one embodiment of the present application, a device for determining input information is provided. The device comprises:
  an acquiring module, configured to acquire target blood-flow information about a first part of a body of a user or a second part that corresponds to the first part, in response to the first part executing an action; and
  a determining module, configured to determine input information according to the target blood-flow information and reference information.

According to the method and device for determining input information in some embodiments of the present application, in response to a first part of a body of a user executing an action, target blood-flow information about the first part or a second part that corresponds to the first part is acquired; and input information is determined according to the target blood-flow information and reference information, thereby affecting the target blood-flow information by means of a body action of a user, and moreover, the input information is determined according to the target blood-flow information. The body of the user is used as an input interface, to cause an interaction area to be increased, which helps to improve input efficiency and user experience.

BRIEF DESCRIPTION OF THE DRAWINGS

FIG. 10 is a schematic diagram of target PPG information detected in a case in which an index finger clicks according to an implementation manner of the present application;

FIG. 11 is a schematic diagram of target PPG information detected in a case in which an index finger double-clicks according to an implementation manner of the present application;

FIG. 12 is a detailed flowchart of step S1412a according to an implementation manner of the present application;

DETAILED DESCRIPTION

The following further describes the specific implementation manners of the present application in detail with reference to the accompanying drawings and embodiments. The following embodiments are used to illustrate the present application, but are not intended to limit the scope of the present application.

It is understood by a person skilled in the art that, in the embodiments of the present application, sequence numbers of the following processes do not mean execution sequences in various embodiments of the present invention. The execution sequences of the processes should be determined according to functions and internal logic of the processes, and should not be construed as any limitation on the implementation processes of the embodiments of the present invention.

It is found by the inventor in a research process that, if a body of a user is in a motion state, acquired blood-flow information comprises a noise produced by motion. Generally, people will attempt to eliminate the noise, so as to improve the accuracy of the acquired blood-flow information.

Meanwhile, it is found by the inventor that, motions of different parts of the body of the user or different motions of a same part of the body of the user produce different noises, may cause the acquired blood-flow information to have different waveform features. Based on this, it may be reasonably inferred which part performs what action according to the obtained blood-flow information, and further, corresponding input information may be determined. The blood-flow information may be PPG (photoelectric plethysmography) information, and may also be Doppler measurement information.

Figure 1:
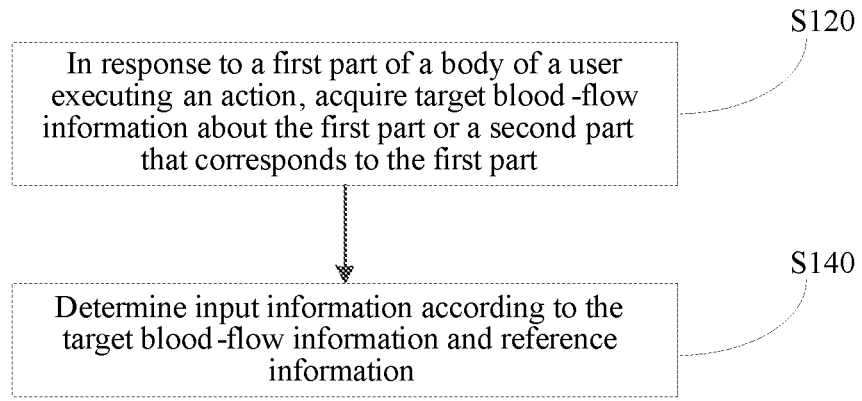
FIG. 1 is a flowchart of a method for determining input information according to an embodiment of the present application.

FIG. 1 is a flowchart of a method for determining input information according to an embodiment of the present application. The method may be implemented by, for example, a device for determining input information. As shown in FIG. 1, the method comprises:

S120: In response to a first part of a body of a user executing an action, acquire target blood-flow information about the first part or a second part that corresponds to the first part.

S140: Determine input information according to the target blood-flow information and reference information.

According to a method in this embodiment of the present application, in response to a first part of a body of a user executing an action, target blood-flow information about the first part or a second part that corresponds to the first part is acquired; and input information is determined according to the target blood-flow information and reference information, thereby affecting the target blood-flow information by means of a body action of a user, and moreover, the input information is determined according to the target blood-flow information. The body of the user is used as an input interface, to cause an interaction area to be increased, which helps to improve input efficiency and user experience.

The following describes functions of the steps S120 and S140 in detail with reference to the specific implementation manners.

S120: In response to a first part of a body of a user executing an action, acquire target blood-flow information about the first part or a second part that corresponds to the first part.

The first part, that is, an action part, for example, may be a finger, a palm, a wrist, a neck, a foot, a leg, and the like of a user. In addition to being used as the action part, the first part may also be used as an acquisition part for target blood-flow information at the same time, for example, in a case in which an acquiring sensor for the target blood-flow information is a smart bracelet, the wrist may be used as the action part and the acquisition part simultaneously.

The second part is another optional acquisition part for the target blood-flow information. Moreover, the second part is a part adjacent to the first part. That is, a distance between the first part and the second part should be less than a distance threshold, for example, the distance is less than 0.1 m. Moreover, it is found by the inventor in the research process that, a shorter distance between the first part and the second part leads to a smaller error of the method. Generally, the first part and the second part are located at a same limb of the user. For example, in a case in which a certain finger is used as the action part, a wrist on the same limb may be used as an acquisition part.

The actions may be some common actions in daily life, such as, a finger clicks, a hand makes a fist, and a palm is stretched out, and may also be some training actions, such as a finger double-clicks fast.

As described above, the blood-flow information may be PPG information or Doppler measurement information. Correspondingly, the target blood-flow information may be target PPG information or target Doppler measurement information.

Figure 2:
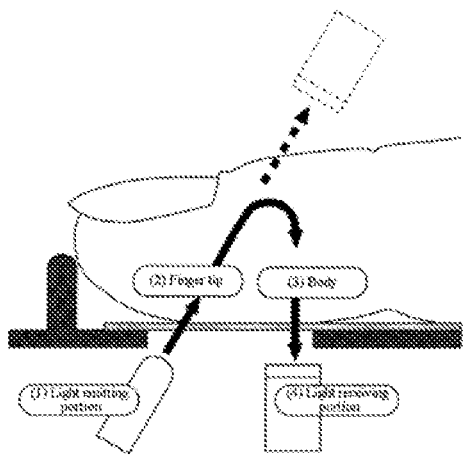
FIG. 2 is a schematic diagram of detecting PPG information according to an implementation manner of the present application.
Figure 3:
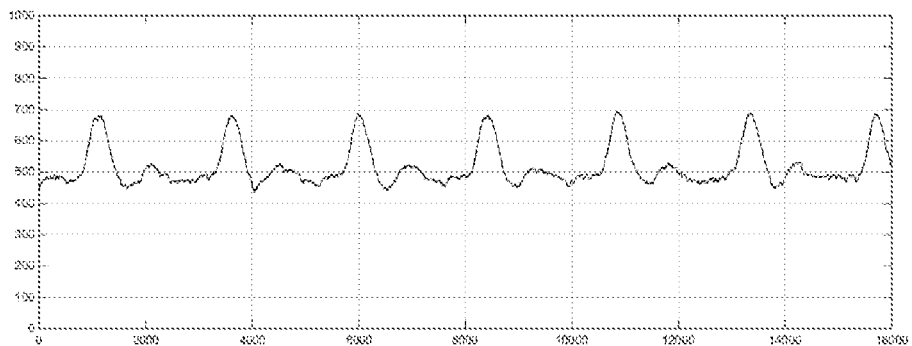
FIG. 3 is a schematic diagram of PPG information detected in a normal case.

FIG. 2 is a schematic diagram of acquiring PPG information about a human body. The principle thereof is that a light receiving portion detects the intensity of reflected light after light emitted by a light emitting portion is reflected by a finger tip. Because blood has a light absorption property, the intensity of the reflected light changes with a change in a flow volume of blood that flows through the finger tip within a unit of time. By measuring a cycle of the change of the reflected light, the PPG information may be obtained, and further, information such as a heart rate may be obtained by calculation. Because hemoglobin in blood has a better absorption effect on green light, generally, a green-light LED may be used as the light emitting portion. In a normal case, a waveform diagram of PPG information as shown in FIG. 3 may be obtained by means of detection.

Figure 4:
FIG. 4 is a schematic diagram of LDF information detected in a normal case.

The Doppler measurement information may be an LDF (Laser Doppler Flowmetry), an LDV (Laser Doppler Velocimety), and an ultrasonic Doppler frequency shift. The implementation principles thereof are similar. LDF information is used as an example, and the acquiring principle thereof is that a laser signal sent by a light emitting unit is detected by a photoelectric sensor after reflection by erythrocyte, and by analyzing a Doppler frequency shift of an electrical signal output by the photoelectric sensor, a flow speed and a blood-flow volume of blood may be measured. An optical blood flow sensor based on the LDF principle may be used to measure a heart rate and the like. In a normal case, a waveform diagram of LDF information as shown in FIG. 4 may be obtained by means of detection.

S140: Determine input information according to the target blood-flow information and reference information.

a) In an implementation manner, the target blood-flow information is target PPG information. Correspondingly, the step S140 is further as follows:

S140a: Determine input information according to the target PPG information and reference information.

In an implementation manner, a first correspondence between the target PPG information and the input information may be directly established, and therefore the input information may be directly determined according to the target PPG information in combination with the reference information.

At the same time, it is understood by a person skilled in the art that, there is further bridge information between the target PPG information and the input information, that is, the first part and/or the action. That is, among the target PPG information, the first part and/or the action, and the input information, there is a second correspondence.

Figure 5:
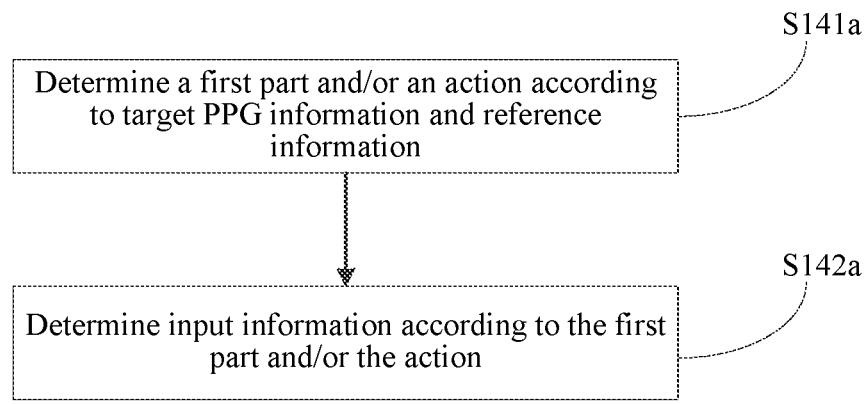
FIG. 5 is a detailed flowchart of step S140a according to an implementation manner of the present application.

Therefore, referring to FIG. 5, in an implementation manner, the step S140a may comprise:

S141a: Determine the first part and/or the action according to the target PPG information and the reference information.

S142a: Determine the input information according to the first part and/or the action.

It is understood by a person skilled in the art that, it may be completely unnecessary for a device to understand the first part and/or the action, that is, the device may perform processing completely based on the first correspondence. However, for clearness, the second correspondence is described in the present application. Because the principles of the first correspondence and the second correspondence are the same, the first correspondence is not respectively described in detail again.

Figure 6:
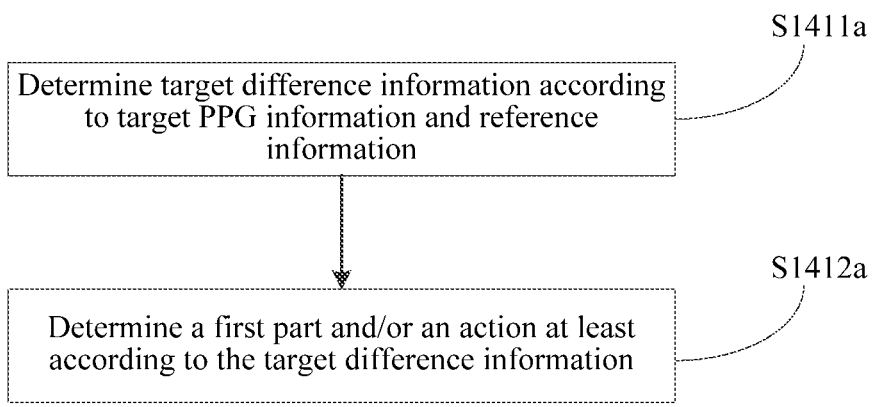
FIG. 6 is a detailed flowchart of step S141a according to an implementation manner of the present application.

Referring to FIG. 6, in an implementation manner, the step S141a may further comprise:

S1411a: Determine target difference information according to the target PPG information and the reference information.

S1412a: Determine the first part and/or the action at least according to the target difference information.

In an implementation manner, in the step S1411a, the reference information may be a first threshold. The first threshold may be set according to PPG information acquired, in a case in which the first part does not execute the action, that is, the first part remains static, from an acquisition part of the target PPG information (PPG information acquired in a normal case for short below), for example, the first threshold is set to a minimum amplitude value of PPG information acquired in a normal case, or a maximum amplitude value of PPG information acquired in a normal case.

Figure 7:
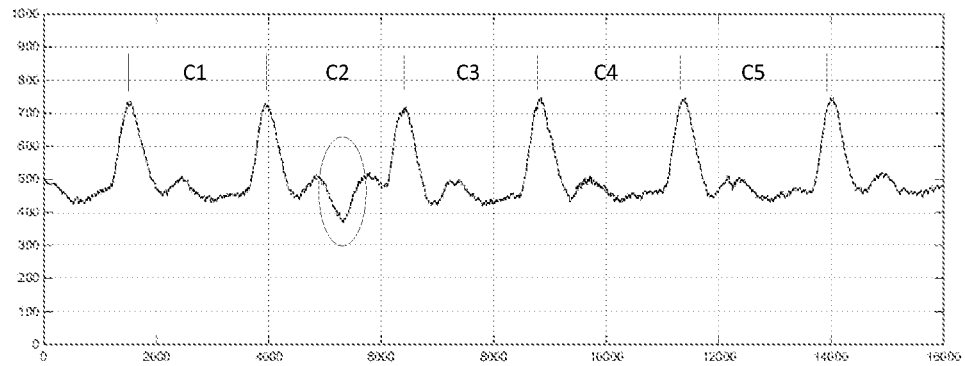
FIG. 7 is a schematic diagram of target PPG information detected in a case in which a middle finger clicks according to an implementation manner of the present application.

The target difference information is a part of the target PPG information, and the action causes the part of the information to be obviously different from the PPG information acquired in a normal case. For example, in a case in which a middle finger clicks, an obtained waveform of the target PPG information is as shown in FIG. 7, where a part, which is within the circle, of the waveform is obviously different from the waveform outside the circle. The part, which is within the circle, of the waveform is a waveform corresponding to the target difference information. The waveform is a waveform formed due to a change in a normal PPG waveform, which is caused by a click performed by the middle finger. It may be seen that, a minimum amplitude value of the part, which is within the circle, of the waveform is obviously lower than an amplitude value of the PPG information acquired in a normal case.

Therefore, in an implementation manner, the step S1411a is further as follows:

S1411a': Compare an amplitude value that is in the target PPG information and a value of the reference information, and determine the target difference information according to a comparison result.

Figure 8:
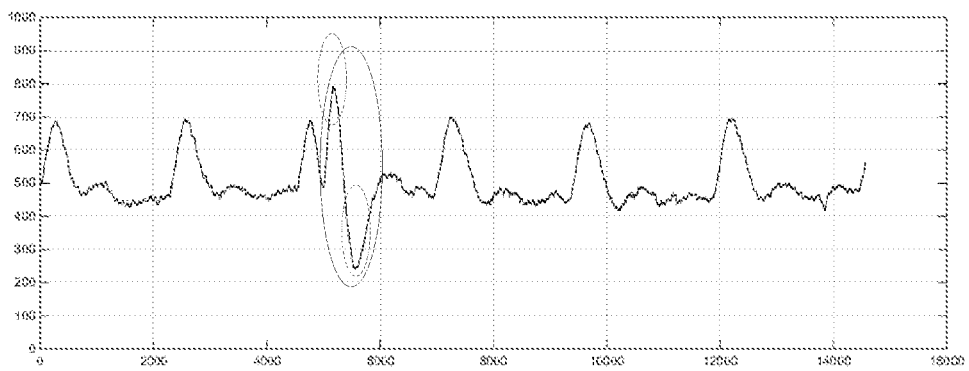
FIG. 8 is a schematic diagram of target PPG information detected in a case in which a fist is made according to an implementation manner of the present application.

Specifically, in a case in which the reference information is a minimum amplitude value of PPG information acquired in a normal case, a part, whose amplitude value is less than the value of the reference information, of the target PPG information may be determined as the target difference information. Certainly, in a case in which the reference information is a maximum amplitude value of PPG information acquired in a normal case, a part, whose amplitude value is greater than the value of the reference information, of the target PPG information may be determined as the target difference information. FIG. 8 is used as an example. FIG. 8 shows a waveform of target PPG information obtained at a wrist in a case in which a fist is made, where the waveform within a circle formed of a solid line is obviously different from the waveform outside the circle formed of the solid line. The waveform within the circle formed of the solid line is a waveform corresponding to the target difference information, and the waveform is a waveform formed due to a change in a normal PPG waveform caused by making of a fist. It may be seen that, a maximum amplitude value of the waveform within the circle formed of the solid line is obviously higher than an amplitude value of the PPG information acquired in a normal case.

It is understood by a person skilled in the art that, for the target PPG information in FIG. 8, target difference information, which is obtained after the target PPG information is processed according to the foregoing step S1411a', may be only the waveforms within two circles formed of dotted lines, that is, an entire waveform within a circle formed of a solid line may not be obtained. However, the waveforms within the two circles formed of dotted lines and other information such as time, may assist in recognizing the action and the action part.

In another implementation manner, in the step S1411a, the reference information may be reference PPG information acquired from an acquisition part of the target PPG information in a case in which the first part does not execute the action, that is, the reference information is PPG information acquired in a normal case. A waveform of the reference PPG information may be as shown in FIG. 3. The waveform may be acquired in advance.

Figure 9:
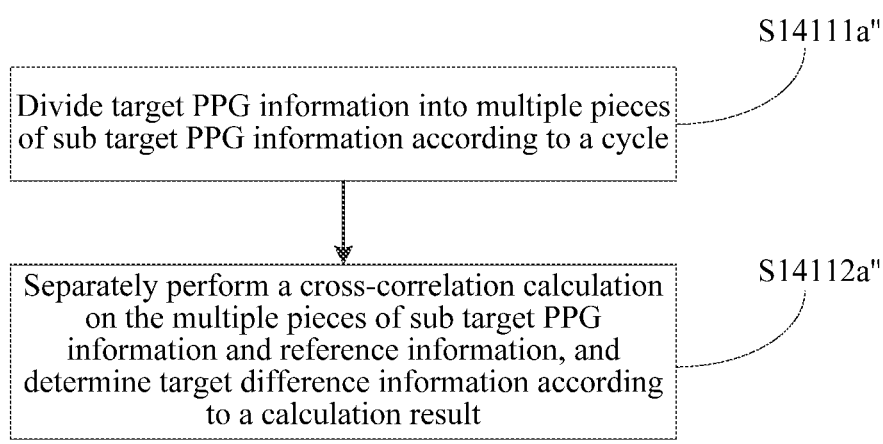
FIG. 9 is a detailed flowchart of the S1411a according to an implementation manner of the present application.

Correspondingly, referring to FIG. 9, in an implementation manner, the step S1411a may comprise:

S14111a": Divide the target PPG information into multiple pieces of sub target PPG information according to a cycle.

S14112a": Respectively perform a cross-correlation calculation on the multiple pieces of sub target PPG information and the reference information, and determine the target difference information according to a calculation result.

The waveform shown in FIG. 7 is still used as an example. In the step S14111a", the waveform shown in FIG. 7 may be divided into C1, C2, C3, C4, and C5 by taking two adjacent wave crests as a cycle. There are five subwaveforms in total. The five subwaveforms are corresponding to five pieces of sub target PPG information. A waveform at edges may be ignored. This is because some extra pieces of PPG information may be acquired during acquiring of the target PPG information.

In the step S14112a", the reference information may be a PPG waveform between two wave crests, which is acquired in a normal case. After a cross-correlation calculation is respectively performed on the five pieces of sub target PPG information and the reference information, it may be found that, a result of a cross-correlation calculation on the reference information and C2 is obviously less than results of cross-correlation calculations on the reference information and the other pieces of sub target PPG information. According to this, it may be determined that PPG information corresponding to C2 is the target difference information.

In an actual application, results of cross-correlation calculations of the reference information and each piece of sub target PPG information may be compared with a threshold, and if a result is less than the threshold, it is determined that a piece of corresponding sub target PPG information is target difference information. The threshold may be, for example, set to 80% of a result of a cross-correlation calculation of the reference information and itself.

It is understood by a person skilled in the art that, the foregoing two manners for determining the target difference information may further be used together, to improve accuracy and efficiency.

In an implementation manner, the step S1412a may further comprise:

S1412a': Determine the action according to the number of wave troughs or wave crests comprised in the target difference information.

The number of wave troughs or wave crests comprised in the target difference information is the same as the number of times that the action is executed. As shown in FIG. 7, in a case in which a middle finger clicks, the corresponding number of wave troughs is 1. As shown in FIG. 8, in a case in which a fist is made once, the corresponding number of wave troughs or wave crests is 1. In addition, FIG. 10 is a waveform of target PPG information, which is obtained in a case in which an index finger clicks. The waveform within a circle is corresponding to the target difference information, and the corresponding number of wave troughs or wave crests of the target difference information is also 1. FIG. 11 is a waveform of target PPG information, which is obtained in a case in which an index finger double-clicks. The waveform within a circle is corresponding to the target difference information. It may be seen that, in this case, the number of wave troughs or wave crests comprised in the target difference information is 2.

In another implementation manner, the step S1412a may further comprise:

S1412a": Determine the action according to a cycle corresponding to the target difference information.

The cycle corresponding to the target difference information is corresponding to a cycle in which the first part executes the action. That is, the longer the first part executes the action each time, the longer the cycle of the target difference information is. Therefore, the cycle corresponding to the target difference information may reflect an execution speed of the action, and therefore the action may be determined. For example, the first part is a foot. If a cycle of an action of raising and putting down the foot is 0.3 s, it may be determined that a corresponding action is walking; and if a cycle of an action of raising and putting down the foot is 0.03 s, it may be determined that a corresponding action is running. Certainly, in a case in which the first part is a hand, it may also be determined whether a user walks or runs according to a cycle of forward and backward swinging of the hand.

In another implementation manner, referring to FIG. 12, the step S1412a may further comprise:

S14121a: Respectively calculate the similarity between a waveform of the target difference information and at least one known waveform, and determine a target known waveform according to a calculation result.

S14122a: Determine the first part and/or the action according to the target known waveform.

The at least one known waveform may be a set of multiple known waveforms and may be obtained by pre-training, for example, the user makes the first part execute different actions in advance and correspondingly acquires waveforms of corresponding target difference information as the known waveforms. Therefore, correspondences among the first part, the action, and the known waveform may be established. The correspondences may be as shown in Table 1.

TABLE 1

| First part | Action | Known waveform |
|---|---|---|
| Index finger | Click | A |
| Index finger | Double-click | B |
| Middle finger | Click | C |

TABLE 1-continued

| First part | Action | Known waveform |
|---|---|---|
| Hand | Make a fist | D |
| Hand | Open | E |

In an actual application, the similarity of a waveform of the target difference information, which is acquired in the step S14121a and each known waveform in the set may be respectively calculated, and then a known waveform of the highest similarity is selected as the target known waveform. Further, in the step S14122a, the first part and/or the action may be determined according to the target known waveform.

A first row in Table 1 is used as example. It is assumed that a waveform of the target difference information is the waveform within a circle as shown in FIG. 10, and it may be obtained by calculation that the waveform of the target difference information is most similar to a known waveform A, and therefore it may be determined that the target known waveform is the known waveform A, and it may further be determined that the first part is an index finger, and an action is click.

In the step S142a, the input information is determined according to the first part and/or the action.

Correspondences between the first part and/or the action and the input information may be predetermined, and the correspondences may be as shown in FIG. 2. A second row is used as an example. It is assumed that a smart bracelet is in communication with smart glasses, the smart bracelet acquires an action instruction of a user and controls the smart glasses, and in a case in which the smart bracelet recognizes an action that an index finger double-clicks, the smart bracelet may control the smart glasses to enable an APP currently presented to the user, for example, enable a camera function. A correspondence table as shown in Table 2 may be pre-stored in a wearable device, such as a smart bracelet, and moreover, such a correspondence table may be provided in an operating instruction of the wearable device, so as to instruct and train a user to perform corresponding command inputting by means of an action similar to an action in Table 2.

TABLE 2

| First part | Action | Input information |
|---|---|---|
| Index finger | Click | Select command |
| Index finger | Double-click | Open command |
| Middle finger | Click | Menu command |
| Hand | Make a fist | Zoom-out command |
| Hand | Open | Zoom-in command |

Figure 13:
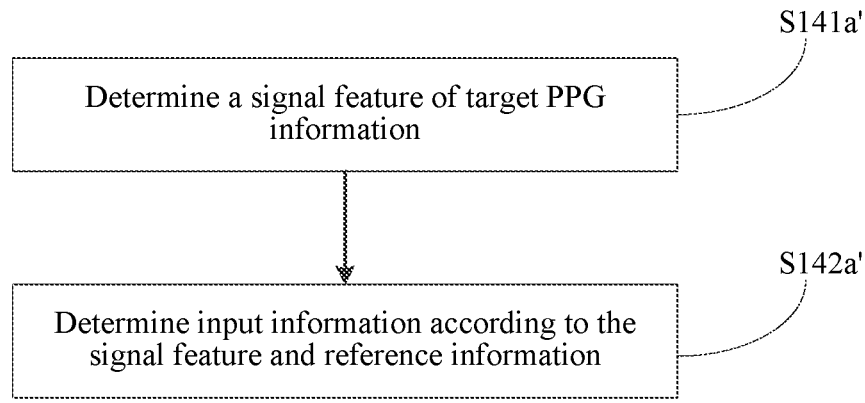
FIG. 13 is a detailed flowchart of the step S140a according to an implementation manner of the present application.

In addition, referring to FIG. 13, in another implementation manner, the step S140a may comprise:

S141a': Determine a signal feature of the target PPG information.

S142a': Determine the input information according to the signal feature and the reference information.

In the step S141a', the signal feature of the target PPG information comprises at least one of a fingerprint, an average value, and a difference of the target PPG information. The fingerprint is formed of at least one of an amplitude, a phase, and a spectrum of the target PPG information; the average value is an average value of at least one of the amplitude, the phase, and the spectrum of the target PPG information; and the difference is a difference of at least one of the amplitude, the phase, and the spectrum of the target PPG information.

In the step S142a', the reference information may be a reference signal feature obtained by pre-training, for example, in a training stage, corresponding actions may be executed according to Table 2, and correspondingly, signal features of corresponding PPG information may be acquired as the reference information. In a specific application, the similarities between the signal feature of the target PPG information and multiple pieces of reference information may be obtained by calculation, and input information corresponding to one reference information having the highest similarity is used as the input information.

b) In another implementation manner, the target blood-flow information is target Doppler measurement information. Correspondingly, the step S140 may further comprise:

S140b: Determine input information according to the target Doppler measurement information and reference information.

The target Doppler measurement information may be, such as, an LDF (Laser Doppler Flowmetry), an LDV (Laser Doppler Velocimety), and an ultrasonic Doppler frequency shift.

Figure 14:
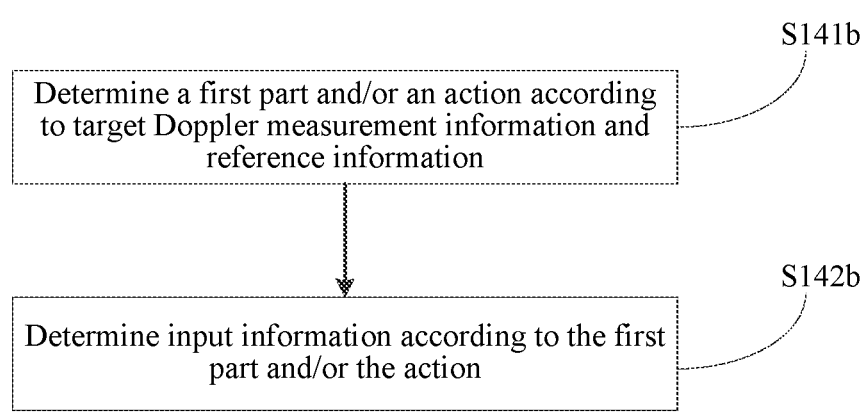
FIG. 14 is a detailed flowchart of step S140b according to an implementation manner of the present application.

Referring to FIG. 14, in an implementation manner, the step S140b may comprise:

S141b: Determine the first part and/or the action according to the target Doppler measurement information and the reference information.

S142b: Determine the input information according to the first part and/or the action.

In an implementation manner, the step S141b may further comprise:

S1411b: Determine target-velocity-related information corresponding to the target Doppler measurement information.

S1412b: Determine the first part and/or the action according to the target-velocity-related information and the reference information.

As described above, the target Doppler measurement information may be, such as, an LDF, an LDV, and an ultrasonic Doppler frequency shift, and comprises a series of envelope wave signals. Corresponding frequency-domain signals may be obtained by performing, for example, a fast Fourier transformation. A Doppler frequency component in the frequency-domain signal is proportionate to a blood-flow speed, and therefore a blood-flow speed may be obtained, and a blood-flow flux may further be determined according to the blood-flow speed and the number of blood cells comprised in a cross section of blood.

A data type of the target-velocity-related information may be the blood-flow speed, and may also be the blood-flow flux. That is, the target-velocity-related information may be target-blood-flow-speed information or target-blood-flow-flux information. Because the target Doppler measurement information comprises a noise caused by the action, the target-velocity-related information also comprises the noise. Specifically, the noise comprises a detection error caused by a change in a blood-flow speed, which is caused by a motion, and a change in the contact between a detection device of the target Doppler measurement information and the limb (different actions cause the contact between the detection device and the limb to change differently). In a common LDF detection process, people generally try to avoid such a noise. However, in the present application, recognition of the action is implemented by using such a noise.

In an implementation manner, the step S1412b may further comprise:

S14121b: Determine target difference information according to the target-velocity-related information and the reference information.

S14122b: Determine the first part and/or the action at least according to the target difference information.

Figure 15:
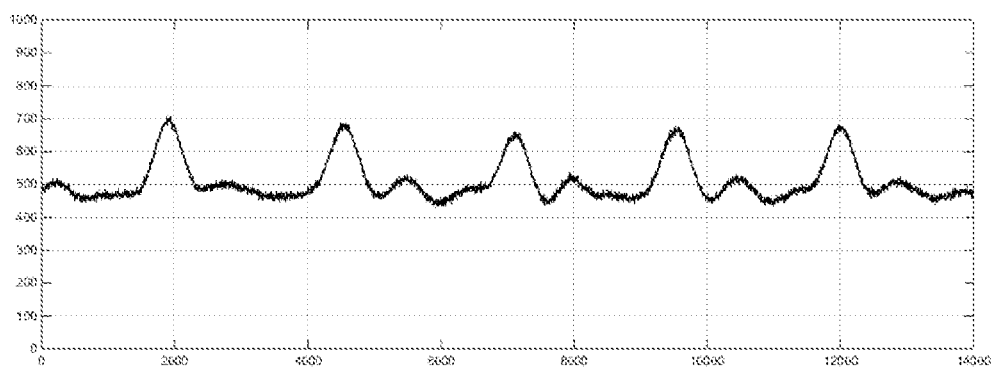
FIG. 15 is a schematic diagram of reference-velocity-related information according to an implementation manner of the present application.

In the step S14121b, the reference information may be of different types. For example, in an implementation manner, the reference information is reference-velocity-related information corresponding to reference Doppler measurement information acquired, in a case in which the first part does not execute the action, from an acquisition part of the target Doppler measurement information. Similar to the target-velocity-related information, the reference-velocity-related information may also be the blood-flow speed or the blood-flow flux. In a case in which the reference-velocity-related information is the blood-flow flux, a waveform thereof may be as shown in FIG. 15. It may be seen that, the blood-flow flux has an obviously cyclical regularity. Information such as a heart rate and a pulse may be obtained according to the waveform.

Correspondingly, the step S14121b may further comprise:

S141211b: Divide the target-velocity-related information into multiple pieces of sub-target-velocity-related information according to a cycle.

S141212b: Respectively perform a cross-correlation calculation on the multiple pieces of sub-target-velocity-related information and the reference information, and determine the target difference information according to a calculation result.

Figure 16:
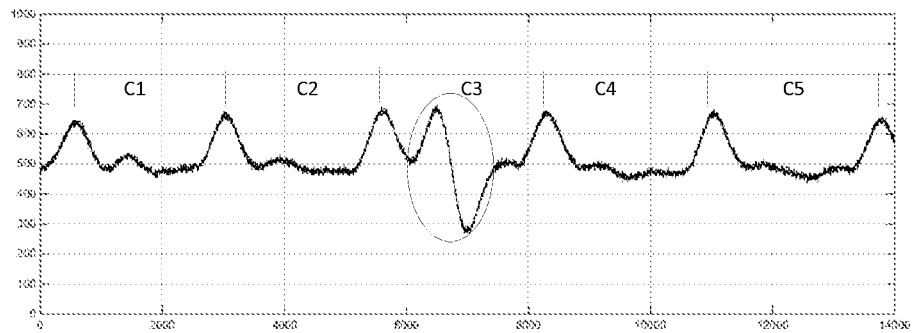
FIG. 16 is a schematic diagram of target-velocity-related information in a case in which an index finger clicks according to an implementation manner of the present application.

In the step S141211b, in a case in which an index finger clicks, an obtained waveform of the target-velocity-related information is as shown in FIG. 16. Five pieces of sub-target-velocity-related information C1, C2, C3, C4, and C5 may be obtained by dividing the waveform according to the cycle. The cycle is the same as a cycle of the reference-velocity-related information.

In the step S141212b, the reference information may be a waveform between two wave crests as shown in FIG. 15. After a cross-correlation calculation is respectively performed on the reference information and the 5 pieces of sub-target-velocity-related information, it may be found that, a result of a cross-correlation calculation on the reference information and C3 is obviously less than results of cross-correlation calculations on the reference information and the other pieces of sub-target-velocity-related information. According to this, it may be determined that sub-target-velocity-related information corresponding to C3 is the target difference information.

In an actual application, results of cross-correlation calculations of the reference information and each piece of sub-target-velocity-related information may be compared with a threshold, and if a result is less than the threshold, it is determined that a piece of corresponding sub-target-velocity-related information is target difference information. The threshold may be, for example, set to 80% of a result of a cross-correlation calculation of the reference information and itself.

In another implementation manner, the reference information may be a first threshold. The first threshold may be set according to an amplitude value of the reference-velocity-related information, for example, the first threshold is set to a minimum amplitude value or a maximum amplitude value of the reference-velocity-related information.

Correspondingly, the step S14121b may further comprise:

S14121b': Compare an amplitude value that is in the target-velocity-related information and a value of the reference information, and determine the target difference information according to a comparison result.

Figure 17:
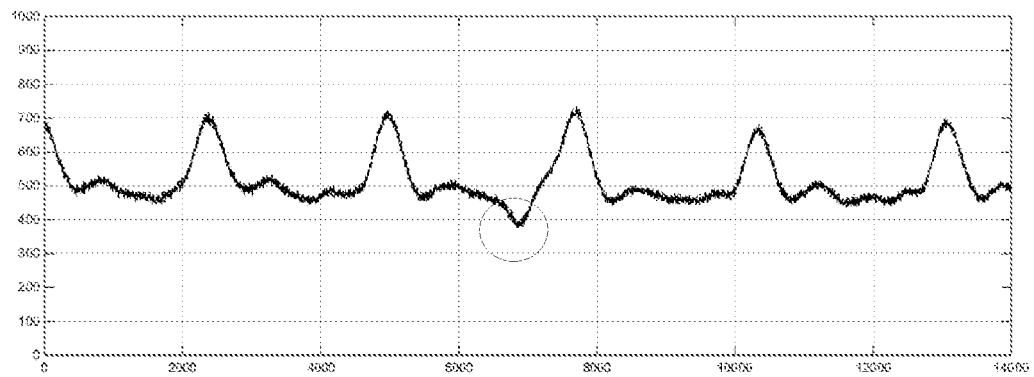
FIG. 17 is a schematic diagram of target-velocity-related information in a case in which a middle finger clicks according to an implementation manner of the present application.

FIG. 17 is used as an example. FIG. 17 shows a waveform of the target-velocity-related information in a case in which a middle finger of the user executes a click action, where the waveform within a circle is obviously different from the waveform outside the circle. The waveform within the circle is a waveform affected by the click action, that is, a waveform corresponding to the target difference information. The reference information, for example, may be set to a minimum amplitude value of the reference-velocity-related information, for example, the reference information is set to 450, and then, the amplitude value in the target-velocity-related information is compared with the amplitude value. It may be seen that, an amplitude value of the waveform within the circle is less than the value of the reference information, and therefore it may be determined that the target difference information is the waveform within the circle.

It is understood by a person skilled in the art that, the foregoing two manners for determining the target difference information may further be used together, to improve accuracy and efficiency.

In the step S14122b, the first part and/or the action is determined at least according to the target difference information. In an implementation manner, the step S14122b may comprise:

S141221b: Respectively calculate the similarity between a waveform of the target difference information and at least one known waveform, and determine a target known waveform according to a calculation result.

S141222b: Determine the first part and/or the action according to the target known waveform.

The at least one known waveform may be a set of multiple known waveforms and may be obtained by pre-training, for example, the user makes the first part execute different actions in advance and correspondingly acquires waveforms of corresponding target difference information as the known waveforms. Therefore, correspondences among the first part, the action, and the known waveform may be established. The correspondences may be as shown in Table 1.

In an actual application, the similarity of a waveform of the target difference information, which is acquired in the step S141221b and each known waveform in the set may be respectively calculated, and then a known waveform of the highest similarity is selected as the target known waveform. Further, in the step S141222b, the first part and/or the action may be determined according to the target known waveform.

A first row in Table 1 is used as example. It is assumed that a waveform of the target difference information is the waveform within a circle as shown in FIG. 16, and it may be obtained by calculation that the waveform of the target difference information is most similar to a known waveform A, and therefore it may be determined that the target known waveform is the known waveform A, and it may further be determined that the first part is an index finger, and an action is click.

In another implementation manner, the step S14122b may be further as follows:

S14122b': Determine the action according to the number of wave troughs or wave crests comprised in the target difference information.

Figure 18:
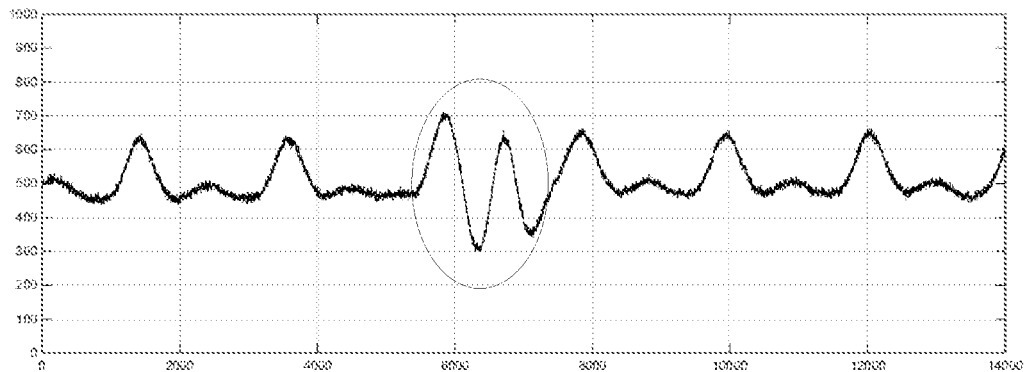
FIG. 18 is a schematic diagram of target-velocity-related information in a case in which an index finger double-clicks according to an implementation manner of the present application.

The number of wave troughs or wave crests comprised in the target difference information is the same with the number of times that the action is executed. As shown in FIG. 17, in a case in which a middle finger clicks, the corresponding number of wave troughs is 1. As shown in FIG. 16, in a case in which an index finger clicks, the corresponding number of wave troughs or wave crests is 1. In addition, FIG. 18 is a waveform of target-velocity-related information, which is obtained in a case in which an index finger double-clicks. The waveform within a circle is corresponding to the target difference information. It may be seen that, in this case, the number of wave troughs or wave crests comprised in the target difference information is 2.

In another implementation manner, the step S14122b may be further as follows:

S14122b": Determine the action according to a cycle corresponding to the target difference information.

The cycle corresponding to the target difference information is corresponding to a cycle in which the first part executes the action. That is, the longer the first part executes the action each time, the longer the cycle of the target difference information is. Therefore, the cycle corresponding to the target difference information may reflect an execution speed of the action, and therefore the action may be determined. For example, the first part is a foot. If a cycle of an action of raising and putting down the foot is 0.3 s, it may be determined that a corresponding action is walking; and if a cycle of an action of raising and putting down the foot is 0.03 s, it may be determined that a corresponding action is running. Certainly, in a case in which the first part is a hand, it may also be determined whether a user walks or runs according to a cycle of forward and backward swinging of the hand.

In the step S142b, the input information is determined according to the first part and/or the action.

Correspondences between the first part and/or the action and the input information may be predetermined, and the correspondences may be as shown in FIG. 2. A correspondence table as shown in Table 2 may be pre-stored in a wearable device, such as a smart bracelet, and moreover, such a correspondence table may be provided in an operating instruction of the wearable device, so as to instruct and train a user to perform corresponding command inputting by means of an action similar to an action in Table 2.

Figure 19:
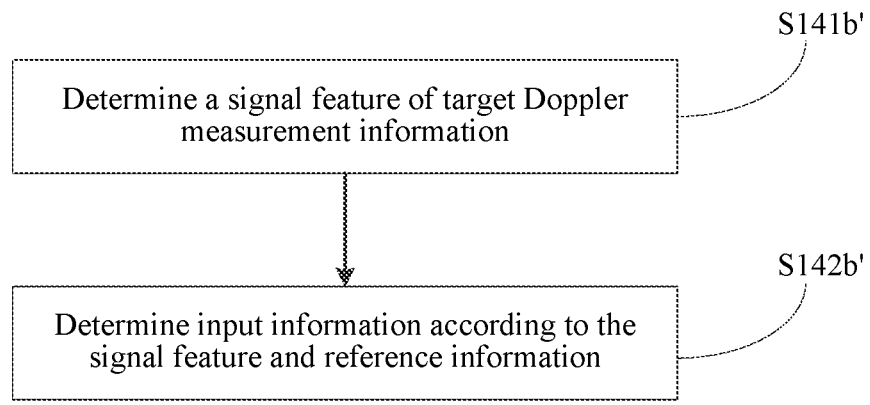
FIG. 19 is a detailed flowchart of the step S140b according to an implementation manner of the present application.

In addition, referring to FIG. 19, in another implementation manner, the step S140b may comprise:

S141b': Determine a signal feature of the target Doppler measurement information.

S142b': Determine the input information according to the signal feature and the reference information.

In the step S141b', the signal feature of the target Doppler measurement information comprises at least one of a fingerprint, an average value, and a difference of the target Doppler measurement information. The fingerprint is formed of at least one of an amplitude, a phase, and a spectrum of the target Doppler measurement information; the average value is an average value of at least one of the amplitude, the phase, and the spectrum of the target Doppler measurement information; and the difference is a difference of at least one of the amplitude, the phase, and the spectrum of the target Doppler measurement information.

In the step S142b', the reference information may be a reference signal feature obtained by pre-training, for example, in a training stage, corresponding actions may be executed according to Table 2, and correspondingly, signal features of corresponding Doppler measurement information may be acquired as the reference information. In a specific application, the similarities between the signal feature of the target Doppler measurement information and multiple pieces of reference information may be obtained by calculation, and input information corresponding to one reference information having the highest similarity is used as the input information.

In an implementation manner, the method may further comprise:

S150: Input the input information.

For example, according to a determining result indicating that the input information is a sleep command, the sleep command is input to a device such as a bracelet or a mobile phone, and the device may switch to a sleep mode according to the sleep command. A device corresponding to the input information may be preset, and certainly, may also be designated by means of the input information.

In addition, the embodiments of the present application further provide a computer readable medium, comprising computer readable instructions for being executed to perform the following operations: operations of steps S120 and S140 in the method in the implementation manner as shown in FIG. 1 are performed.

In conclusion, according to the methods in the embodiments of the present application, a body of a user may be used as an input interface to input information to a corresponding electronic device, thereby improving input capability of a wearable device and the like and improving user experience.

Figure 20:
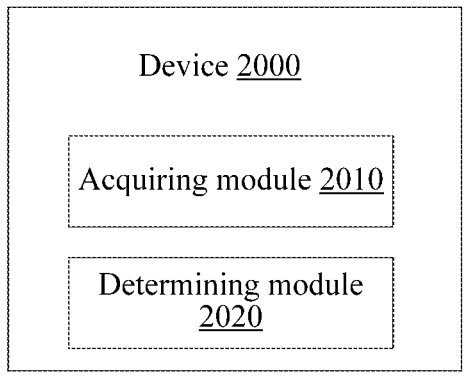
FIG. 20 is a schematic structural diagram of modules of a device for determining input information according to an embodiment of the present application.

FIG. 20 is a schematic structural diagram of modules of a device for determining input information according to an embodiment of the present application. The device for determining input information may be disposed in a wearable device such as a smart wristband or a smart watch as a functional module, and certainly, may also be used by a user as an independent wearable device. As shown in FIG. 20, the device 2000 may comprise:

an acquiring module 2010, configured to acquire target blood-flow information about a first part of a body of a user or a second part that corresponds to the first part, in response to the first part executing an action; and a determining module 2020, configured to determine input information according to the target blood-flow information and reference information.

According to the device in some embodiments of the present application, in response to a first part of a body of a user executing an action, target blood-flow information about the first part or a second part that corresponds to the first part is acquired; and input information is determined according to the target blood-flow information and reference information, thereby affecting the target blood-flow information by means of a body action of a user, and moreover, the input information is determined according to the target blood-flow information. The body of the user is used as an input interface, to cause an interaction area to be increased, which helps to improve input efficiency and user experience.

The following describes functions of the acquiring module 2010 and the determining module 2020 in detail with reference to the specific implementation manners.

The acquiring module 2010 is configured to acquire target blood-flow information about a first part of a body of a user or a second part that corresponds to the first part, in response to the first part executing an action.

The first part, that is, an action part, for example, may be a finger, a palm, a wrist, a neck, a foot, a leg, and the like of a user. In addition to being used as the action part, the first part may also be used as an acquisition part for target blood-flow information at the same time, for example, in a case in which an acquiring sensor for the target blood-flow information is a smart bracelet, the wrist may be used as the action part and the acquisition part simultaneously.

The second part is another optional acquisition part for the target blood-flow information. Moreover, the second part is a part adjacent to the first part. That is, a distance between the first part and the second part should be less than a distance threshold, for example, the distance is less than 0.1 m. Moreover, it is found by the inventor in the research process that, a shorter distance between the first part and the second part leads to a smaller error of the method. Generally, the first part and the second part are located at a same limb of the user. For example, in a case in which the finger is used as the action part, the wrist on the same limb may be used as an acquisition part.

The actions may be some common actions in daily life, such as, a finger clicks, a hand makes a fist, and a palm is stretched out, and may also be some training actions, such as a finger double-clicks fast.

As described above, the blood-flow information may be PPG information or Doppler measurement information. Correspondingly, the target blood-flow information may be target PPG information or target Doppler measurement information.

The determining module 2020 is configured to determine input information according to the target blood-flow information and reference information.

a) In an implementation manner, the target blood-flow information is target PPG information. Correspondingly, the determining module 2020 is configured to determine input information according to the target PPG information and reference information.

In an implementation manner, a first correspondence between the target PPG information and the input information may be directly established, and therefore the input information may be directly determined according to the target PPG information in combination with the reference information.

Figure 21:
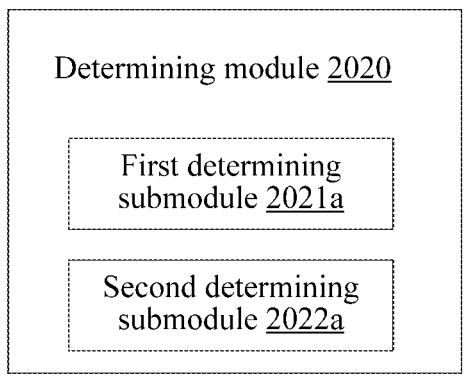
FIG. 21 is a schematic structural diagram of modules of the determining module according to an implementation manner of the present application.

In another implementation manner, referring to FIG. 21, the determining module 2020 may comprise:
  a first determining submodule 2021a, configured to determine the first part and/or the action according to the target PPG information and the reference information; and
  a second determining submodule 2022a, configured to determine the input information according to the first part and/or the action.

Figure 22:
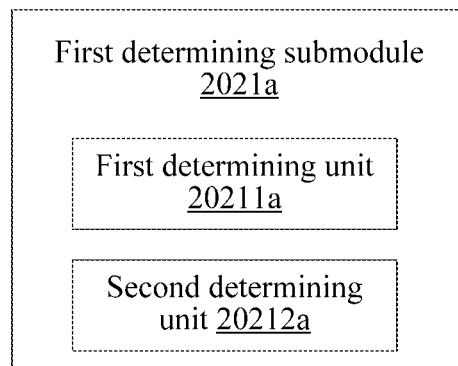
FIG. 22 is a schematic structural diagram of modules of the first determining submodule according to an implementation manner of the present application.

In an implementation manner, referring to FIG. 22, the first determining submodule 2021a comprises:
  a first determining unit 20211a, configured to determine target difference information according to the target PPG information and the reference information; and
  a second determining unit 20212a, configured to determine the first part and/or the action at least according to the target difference information.

In an implementation manner, the reference information may be a first threshold. The first threshold may be set according to PPG information acquired, in a case in which the first part does not execute the action, that is, the first part remains static, from an acquisition part of the target PPG information (PPG information acquired in a normal case for short below), for example, the first threshold is set to a minimum amplitude value of PPG information acquired in a normal case, or a maximum amplitude value of PPG information acquired in a normal case.

The target difference information is a part of the target PPG information, and the action causes the part of the information to be obviously different from the PPG information acquired in a normal case. For example, in a case in which a middle finger clicks, an obtained waveform of the target PPG information is as shown in FIG. 7, where the part, which is within the circle, of the waveform is obviously different from the waveform outside the circle. The part, which is within the circle, of the waveform is a waveform corresponding to the target difference information. The waveform is a waveform formed due to a change in a normal PPG waveform, which is caused by a click performed by the middle finger. It may be seen that, a minimum amplitude value of the part, which is within the circle, of the waveform is obviously lower than an amplitude value of the PPG information acquired in a normal case.

Therefore, in an implementation manner, the first determining unit 20211a is configured to compare an amplitude value that is in the target PPG information and a value of the reference information, and determine the target difference information according to a comparison result.

Specifically, in a case in which the reference information is a minimum amplitude value of PPG information acquired in a normal case, a part, whose amplitude value is less than the value of the reference information, of the target PPG information may be determined as the target difference information. Certainly, in a case in which the reference information is a maximum amplitude value of PPG information acquired in a normal case, a part, whose amplitude value is greater than the value of the reference information, of the target PPG information may be determined as the target difference information. FIG. 8 is used as an example. FIG. 8 shows a waveform of target PPG information obtained at a wrist in a case in which a fist is made, where the waveform within a circle formed of a solid line is obviously different from the waveform outside the circle formed of the solid line. The waveform within the circle formed of the solid line is a waveform corresponding to the target difference information, and the waveform is a waveform formed due to a change in a normal PPG waveform caused by making of a fist. It may be seen that, a maximum amplitude value of the waveform within the circle formed of the solid line is obviously higher than an amplitude value of the PPG information acquired in a normal case.

In another implementation manner, the reference information may be reference PPG information acquired from an acquisition part of the target PPG information in a case in which the first part does not execute the action, that is, the reference information is PPG information acquired in a normal case. A waveform of the reference PPG information may be as shown in FIG. 3. The waveform may be acquired in advance.

Figure 23:
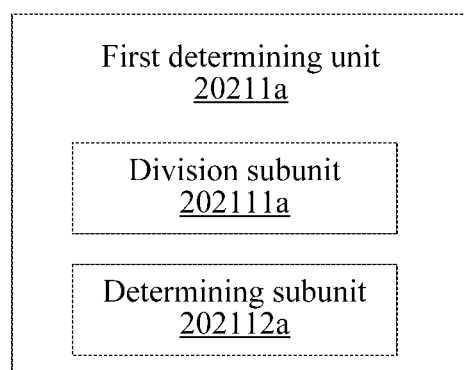
FIG. 23 is a schematic structural diagram of modules of the first determining unit according to an implementation manner of the present application.

Correspondingly, referring to FIG. 23, in an implementation manner, the first determining unit 20211a comprises:
  a division subunit 202111a, configured to divide the target PPG information into multiple pieces of sub target PPG information according to a cycle; and
  a determining subunit 202112a, configured to respectively perform a cross-correlation calculation on the multiple pieces of sub target PPG information and the reference information, and determine the target difference information according to a calculation result.

The waveform shown in FIG. 7 is still used as an example. The division subunit 202111a may divide the waveform shown in FIG. 7 into C1, C2, C3, C4, and C5 by taking two adjacent wave crests as a cycle. There are five subwaveforms in total. The five subwaveforms are corresponding to five pieces of sub target PPG information. A waveform at edges may be ignored. This is because some extra pieces of PPG information may be acquired during acquiring of the target PPG information.

In the determining subunit 202112a, the reference information may be a PPG waveform between two wave crests, which is acquired in a normal case. After a cross-correlation calculation is respectively performed on the five pieces of sub target PPG information and the reference information, it may be found that, a result of a cross-correlation calculation on the reference information and C2 is obviously less than results of cross-correlation calculations on the reference information and the other pieces of sub target PPG information. According to this, it may be determined that PPG information corresponding to C2 is the target difference information.

In an actual application, results of cross-correlation calculations of the reference information and each piece of sub target PPG information may be compared with a threshold, and if a result is less than the threshold, it is determined that a piece of corresponding sub target PPG information is target difference information. The threshold may be, for example, set to 80% of a result of a cross-correlation calculation of the reference information and itself.

It is understood by a person skilled in the art that, the foregoing two manners for determining the target difference information may further be used together, to improve accuracy and efficiency.

In an implementation manner, the second determining unit 20212a is configured to determine the action according to the number of wave troughs or wave crests comprised in the target difference information.

The number of wave troughs or wave crests comprised in the target difference information is the same with the number of times that the action is executed. As shown in FIG. 7, in a case in which a middle finger clicks, the corresponding number of wave troughs is 1. As shown in FIG. 8, in a case in which a fist is made once, the corresponding number of wave troughs or wave crests is 1. In addition, FIG. 10 is a waveform of target PPG information, which is obtained in a case in which an index finger clicks. The waveform within a circle is corresponding to the target difference information, and the corresponding number of wave troughs or wave crests of the target difference information is also 1. FIG. 11 is a waveform of target PPG information, which is obtained in a case in which an index finger double-clicks. The waveform within a circle is corresponding to the target difference information. It may be seen that, in this case, the number of wave troughs or wave crests comprised in the target difference information is 2.

In another implementation manner, the second determining unit 20212a is configured to determine the action according to a cycle corresponding to the target difference information.

The cycle corresponding to the target difference information is corresponding to a cycle in which the first part executes the action. That is, the longer the first part executes the action each time, the longer the cycle of the target difference information is. Therefore, the cycle corresponding to the target difference information may reflect an execution speed of the action, and therefore the action may be determined. For example, the first part is a foot. If a cycle of an action of raising and putting down the foot is 0.3 s, it may be determined that a corresponding action is walking; and if a cycle of an action of raising and putting down the foot is 0.03 s, it may be determined that a corresponding action is running. Certainly, in a case in which the first part is a hand, it may also be determined whether a user walks or runs according to a cycle of forward and backward swinging of the hand.

Figure 24:
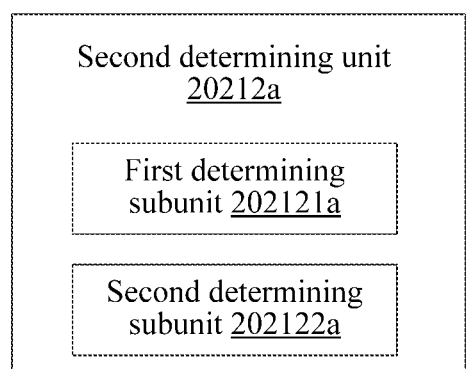
FIG. 24 is a schematic structural diagram of modules of the second determining unit according to an implementation manner of the present application.

In another implementation manner, referring to FIG. 24, the second determining unit 20212a comprises:
a first determining subunit 202121a, configured to respectively calculate the similarity between a waveform of the target difference information and at least one known waveform, and determine a target known waveform according to a calculation result; and
a second determining subunit 202122a, configured to determine the first part and/or the action according to the target known waveform.

The at least one known waveform may be a set of multiple known waveforms and may be obtained by pre-training, for example, the user makes the first part execute different actions in advance and correspondingly acquires waveforms of corresponding target difference information as the known waveforms. Therefore, correspondences among the first part, the action, and the known waveform may be established. The correspondences may be as shown in Table 1.

In an actual application, the similarity of a waveform of the target difference information and each known waveform in the set may be respectively calculated, and then a known waveform of the highest similarity is selected as the target known waveform. Further, the first part and/or the action may be determined according to the target known waveform.

The second determining submodule 2022a is configured to determine the input information according to the first part and/or the action.

Correspondences between the first part and/or the action and the input information may be predetermined, and the correspondences may be as shown in FIG. 2. A second row is used as an example. It is assumed that a smart bracelet is in communication with smart glasses, the smart bracelet acquires an action instruction of a user and controls the smart glasses, and in a case in which the smart bracelet recognizes an action that an index finger double-clicks, the smart bracelet may control the smart glasses to enable an APP currently presented to the user, for example, enable a camera function. A correspondence table as shown in Table 2 may be pre-stored in a wearable device, such as a smart bracelet, and moreover, such a correspondence table may be provided in an operating instruction of the wearable device, so as to instruct and train a user to perform corresponding command inputting by means of an action similar to an action in Table 2.

Figure 25:
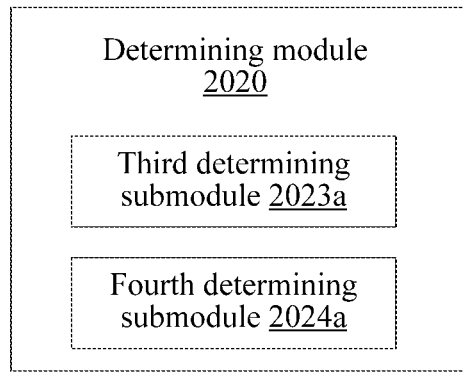
FIG. 25 is a schematic structural diagram of modules of the determining module according to an implementation manner of the present application.

In addition, referring to FIG. 25, in an implementation manner, the determining module 2020 comprises:
a third determining submodule 2023a, configured to determine a signal feature of the target PPG information; and
a fourth determining submodule 2024a, configured to determine the input information according to the signal feature and the reference information.

The signal feature of the target PPG information comprises at least one of a fingerprint, an average value, and a difference of the target PPG information. The fingerprint is formed of at least one of an amplitude, a phase, and a spectrum of the target PPG information; the average value is an average value of at least one of the amplitude, the phase, and the spectrum of the target PPG information; and the difference is a difference of at least one of the amplitude, the phase, and the spectrum of the target PPG information.

The reference information may be a reference signal feature obtained by pre-training, for example, in a training stage, corresponding actions may be executed according to Table 2, and correspondingly, signal features of corresponding PPG information may be acquired as the reference information. In a specific application, the similarities between the signal feature of the target PPG information and multiple pieces of reference information may be obtained by calculation, and input information corresponding to one reference information having the highest similarity is used as the input information.

b) In another implementation manner, the target blood-flow information is target Doppler measurement information. Correspondingly, the determining module 2020 is configured to determine input information according to the target Doppler measurement information and reference information.

Figure 26:
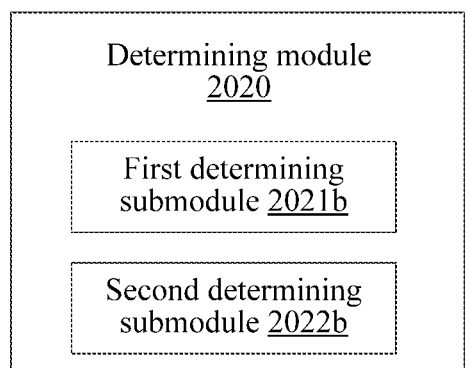
FIG. 26 is a schematic structural diagram of modules of the determining module according to an implementation manner of the present application.

In an implementation manner, referring to FIG. 26, the determining module 2020 comprises:
 a first determining submodule 2021b, configured to determine the first part and/or the action according to the target Doppler measurement information and the reference information; and
 a second determining submodule 2022b, configured to determine the input information according to the first part and/or the action.

Figure 27:
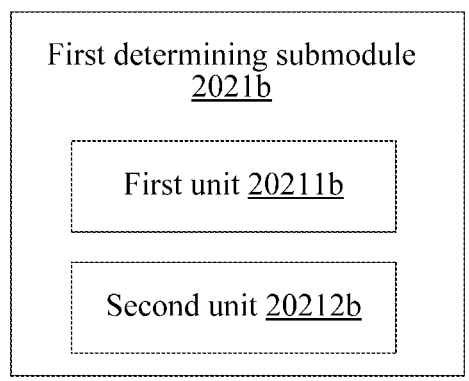
FIG. 27 is a schematic structural diagram of modules of the first determining submodule according to an implementation manner of the present application.

In an implementation manner, referring to FIG. 27, the first determining submodule 2021b comprises:
 a first unit 20211b, configured to determine target-velocity-related information corresponding to the target Doppler measurement information; and
 a second unit 20212b, configured to determine the first part and/or the action according to the target-velocity-related information and the reference information.

A data type of the target-velocity-related information may be the blood-flow speed, and may also be the blood-flow flux. That is, the target-velocity-related information may be target-blood-flow-speed information or target-blood-flow-flux information. Because the target Doppler measurement information comprises a noise caused by the action, the target-velocity-related information also comprises the noise. Specifically, the noise comprises a detection error caused by a change in a blood-flow speed, which is caused by a motion, and a change in a detection device of the target Doppler measurement information and limb touch. In a common LDF detection process, people generally try to avoid such a noise. However, in the present application, recognition of the action is implemented by using such a noise.

Figure 28:
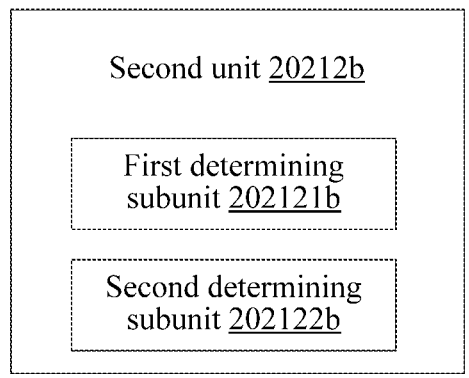
FIG. 28 is a schematic structural diagram of modules of the second unit according to an implementation manner of the present application.

In an implementation manner, referring to FIG. 28, the second unit 20212b comprises:
 a first determining subunit 202121b, configured to determine target difference information according to the target-velocity-related information and the reference information; and
 a second determining subunit 202122b, configured to determine the first part and/or the action at least according to the target difference information.

The reference information may be of different types. For example, in an implementation manner, the reference information is reference-velocity-related information corresponding to reference Doppler measurement information acquired, in a case in which the first part does not execute the action, from an acquisition part of the target Doppler measurement information. Similar to the target-velocity-related information, the reference-velocity-related information may also be the blood-flow speed or the blood-flow flux. In a case in which the reference-velocity-related information is the blood-flow flux, a waveform thereof may be as shown in FIG. 15. It may be seen that, the blood-flow flux has an obviously cyclical regularity. Information such as a heart rate and a pulse may be obtained according to the waveform.

Figure 29:
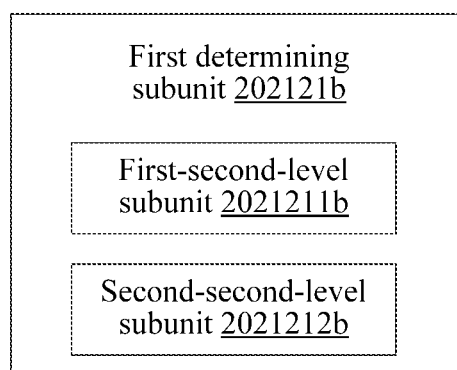
FIG. 29 is a schematic structural diagram of modules of the first determining subunit according to an implementation manner of the present application.

Correspondingly, in an implementation manner, referring to FIG. 29, the first determining subunit 202121b comprises:
 a first-second-level subunit 2021211b, configured to divide the target-velocity-related information into multiple pieces of sub-target-velocity-related information according to a cycle; and
 a second-second-level subunit 2021212b, configured to respectively perform a cross-correlation calculation on the multiple pieces of sub-target-velocity-related information and the reference information, and determine the target difference information according to a calculation result.

For example, in a case in which an index finger clicks, an obtained waveform of the target-velocity-related information is as shown in FIG. 16. Five pieces of sub-target-velocity-related information C1, C2, C3, C4, and C5 may be obtained by dividing the waveform according to the cycle. The cycle is the same as a cycle of the reference-velocity-related information.

The reference information may be a waveform between two wave crests as shown in FIG. 15. After a cross-correlation calculation is respectively performed on the reference information and the 5 pieces of sub-target-velocity-related information, it may be found that, a result of a cross-correlation calculation on the reference information and C3 is obviously less than results of cross-correlation calculations on the reference information and the other pieces of sub-target-velocity-related information. According to this, it may be determined that sub-target-velocity-related information corresponding to C3 is the target difference information.

In an actual application, results of cross-correlation calculations of the reference information and each piece of sub-target-velocity-related information may be compared with a threshold, and if a result is less than the threshold, it is determined that a piece of corresponding sub-target-velocity-related information is target difference information. The threshold may be, for example, set to 80% of a result of a cross-correlation calculation of the reference information and itself.

In another implementation manner, the reference information may be a first threshold. The first threshold may be set according to an amplitude value of the reference-velocity-related information, for example, the first threshold is set to a minimum amplitude value or a maximum amplitude value of the reference-velocity-related information.

Correspondingly, the first determining subunit 202121b is configured to compare an amplitude value that is in the target-velocity-related information and a value of the reference information, and determine the target difference information according to a comparison result.

FIG. 17 is used as an example. FIG. 17 shows a waveform of the target-velocity-related information in a case in which a middle finger of the user executes a click action, where the waveform within a circle is obviously different from the waveform outside the circle. The waveform within the circle is a waveform affected by the click action, that is, a waveform corresponding to the target difference information. The reference information, for example, may be set to a minimum amplitude value of the reference-velocity-related information, for example, the reference information is set to 450, and then, the amplitude value in the target-velocity-related information is compared with the amplitude value. It may be seen that, an amplitude value of the waveform within the circle is less than the value of the reference information, and therefore it may be determined that the target difference information is the waveform within the circle.

It is understood by a person skilled in the art that, the foregoing two manners for determining the target difference information may further be used together, to improve accuracy and efficiency.

The second determining subunit 202122b is configured to determine the first part and/or the action at least according to the target difference information.

Figure 30:
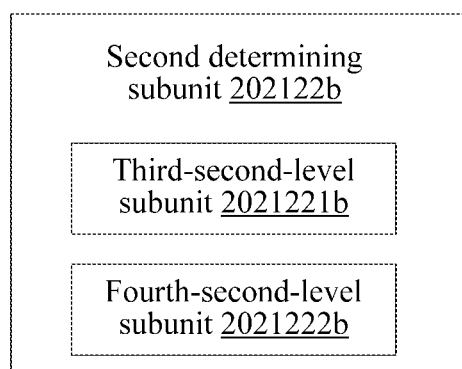
FIG. 30 is a schematic structural diagram of modules of the second determining subunit according to an implementation manner of the present application.

In an implementation manner, referring to FIG. 30, the second determining subunit 202122b comprises:

- a third-second-level subunit 2021221b, configured to respectively calculate the similarity between a waveform of the target difference information and at least one known waveform, and determine a target known waveform according to a calculation result; and
- a fourth-second-level subunit 2021222b, configured to determine the first part and/or the action according to the target known waveform.

The at least one known waveform may be a set of multiple known waveforms and may be obtained by pre-training, for example, the user makes the first part execute different actions in advance and correspondingly acquires waveforms of corresponding target difference information as the known waveforms. Therefore, correspondences among the first part, the action, and the known waveform may be established. The correspondences may be as shown in Table 1.

In an actual application, the similarity of a waveform of the target difference information and each known waveform in the set may be respectively calculated, and then a known waveform of the highest similarity is selected as the target known waveform. Further, the first part and/or the action may be determined according to the target known waveform.

A first row in Table 1 is used as example. It is assumed that a waveform of the target difference information is the waveform within a circle as shown in FIG. 16, and it may be obtained by calculation that the waveform of the target difference information is most similar to a known waveform A, and therefore it may be determined that the target known waveform is the known waveform A, and it may further be determined that the first part is an index finger, and an action is click.

In another implementation manner, the second determining subunit 202122b is configured to determine the action according to the number of wave troughs or wave crests comprised in the target difference information.

The number of wave troughs or wave crests comprised in the target difference information is the same with the number of times that the action is executed. As shown in FIG. 17, in a case in which a middle finger clicks, the corresponding number of wave troughs is 1. As shown in FIG. 16, in a case in which an index finger clicks, the corresponding number of wave troughs or wave crests is 1. In addition, FIG. 18 is a waveform of target-velocity-related information, which is obtained in a case in which an index finger double-clicks. The waveform within a circle is corresponding to the target difference information. It may be seen that, in this case, the number of wave troughs or wave crests comprised in the target difference information is 2.

In another implementation manner, the second determining subunit 202122b is configured to determine the action according to a cycle corresponding to the target difference information.

The cycle corresponding to the target difference information is corresponding to a cycle in which the first part executes the action. That is, the longer the first part executes the action each time, the longer the cycle of the target difference information is. Therefore, the cycle corresponding to the target difference information may reflect an execution speed of the action, and therefore the action may be determined. For example, the first part is a foot. If a cycle of an action of raising and putting down the foot is 0.3 s, it may be determined that a corresponding action is walking; and if a cycle of an action of raising and putting down the foot is 0.03 s, it may be determined that a corresponding action is running. Certainly, in a case in which the first part is a hand, it may also be determined whether a user walks or runs according to a cycle of forward and backward swinging of the hand.

The second determining submodule 2022b, configured to determine the input information according to the first part and/or the action.

Correspondences between the first part and/or the action and the input information may be predetermined, and the correspondences may be as shown in FIG. 2. A correspondence table as shown in Table 2 may be pre-stored in a wearable device, such as a smart bracelet, and moreover, such a correspondence table may be provided in an operating instruction of the wearable device, so as to instruct and train a user to perform corresponding command inputting by means of an action similar to an action in Table 2.

Figure 31:
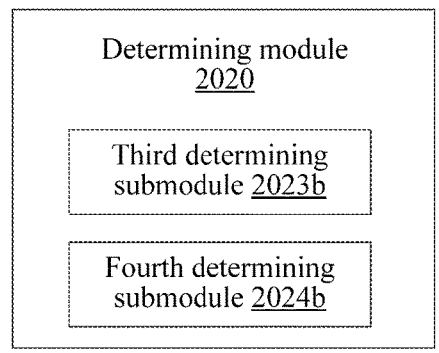
FIG. 31 is a schematic structural diagram of modules of the determining module according to an implementation manner of the present application.

In addition, referring to FIG. 31, in an implementation manner, the determining module 2020 comprises:

- a third determining submodule 2023b, configured to determine a signal feature of the target Doppler measurement information; and
- a fourth determining submodule 2024b, configured to determine the input information according to the signal feature and the reference information.

The signal feature of the target Doppler measurement information comprises at least one of a fingerprint, an average value, and a difference of the target Doppler measurement information. The fingerprint is formed of at least one of an amplitude, a phase, and a spectrum of the target Doppler measurement information; the average value is an average value of at least one of the amplitude, the phase, and the spectrum of the target Doppler measurement information; and the difference is a difference of at least one of the amplitude, the phase, and the spectrum of the target Doppler measurement information.

The reference information may be a reference signal feature obtained by pre-training, for example, in a training stage, corresponding actions may be executed according to Table 2, and correspondingly, signal features of corresponding Doppler measurement information may be acquired as the reference information. In a specific application, the similarities between the signal feature of the target Doppler measurement information and multiple pieces of reference information may be obtained by calculation, and input information corresponding to one reference information having the highest similarity is used as the input information.

An application scenario of the method and device for determining input information according to the embodiments of the present application may be as follows: A left wrist of a user wears a smart bracelet; when the user wants to know current time, the user quickly clicks a desktop twice by using an index finger of a left hand, the bracelet recognizes that the index finger of the left hand of the user executes a double-click action by detecting a change in blood-flow information about the left wrist, and determines that corresponding input information is a time-displayed command, and therefore, the command is input to a control module, and the control module inputs the current time in a voice manner by controlling the bracelet; and when the user wants the bracelet to sleep, the user quickly clicks a desktop type by using a middle finger of a left hand, the bracelet recognizes that the middle finger of the left hand executes a double-click action by detecting a change in blood-flow information about a left wrist, and determines that corresponding input information is a sleep command, and therefore, the command is input to the control module, and the control module controls the bracelet to switch to a sleep mode.

Figure 32:
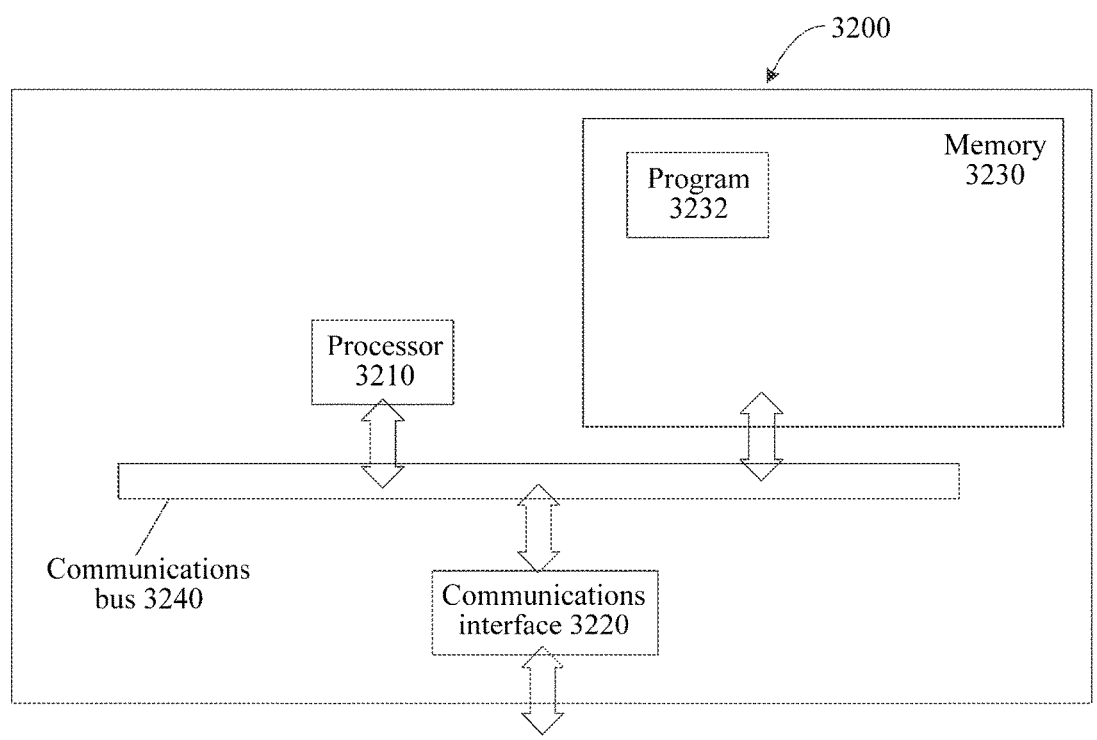
FIG. 32 is a schematic structural diagram of hardware of a device for determining input information according to an implementation manner of the present application.

A hardware structure of a device for determining input information according to another embodiment of the present application is as shown in FIG. 32. Specific implementation of the device for determining input information is not limited in a specific embodiment of the present application. Referring to FIG. 32, the device 3200 may comprise:

a processor 3210, a communications interface 3220, a memory 3230, and a communications bus 3240.

The processor 3210, the communications interface 3220, and the memory 3230 communicate with each other through the communications bus 3240.

The communications interface 3220 is configured to communicate with another network element.

The processor 3210 is configured to execute a program 3232, and specifically, may execute a related step in the embodiments of the method shown in FIG. 1.

Specifically, the program 3232 may comprise program codes. The program codes comprises computer operation instructions.

The processor 3210 may be a central processing unit (CPU) or an application specific integrated circuit (ASIC), or may be configured as one or more integrated circuits that implement the embodiments of the present application.

The memory 3230 is configured to store the program 3232. The memory 3230 may comprise a random access memory (RAM), and may also comprise a non-volatile memory, for example, at least one magnetic disk storage. The processor 3232 may specifically execute the following steps:

in response to a first part of a body of a user executing an action, target blood-flow information about the first part or a second part that corresponds to the first part is acquired; and input information is determined according to the target blood-flow information and reference information.

Reference can be made to corresponding steps or modules in the embodiments for specific implementation of the steps in the program 3232, which is not repeated herein. A person skilled in the art may clearly understand that, reference can be made to the corresponding process description in the method embodiments for the device described above and the specific working procedures of the modules, and will not be repeated herein in order to make the description convenient and concise.

It can be appreciated by those of ordinary skill in the art that, exemplary units and method steps described with reference to the embodiments disclosed in this specification can be implemented by electronic hardware or a combination of computer software and electronic hardware. Whether these functions are executed by hardware or software depends on specific applications and design constraints of the technical solution. A person skilled in the art may use different methods to implement the described functions for a specific application, but such implementation should not be construed as a departure from the scope of the present application.

If the function is implemented in the form of a software functional unit and is sold or used as an independent product, the product can be stored in a non-transitory computer-readable storage medium. Based on such understanding, the technical solution of the present application essentially, or the part that contributes to the prior art, or a part of the technical solution may be embodied in the form of a software product; the computer software product is stored in a storage medium and comprises several instructions for enabling a computer device (which may be a personal computer, a server, a network device, or the like) to execute all or some of the steps of the method in the embodiments of the present application. The foregoing storage medium comprises various mediums capable of storing program code, such as, a USB flash drive, a removable hard disk, a read-only memory (ROM), a random access memory (RAM), a magnetic disk, or an optical disc.

The foregoing implementation manners are only used to describe the present application, but not to limit the present application. A person of ordinary skill in the art can still make various alterations and modifications without departing from the spirit and scope of the present application; therefore, all equivalent technical solutions also fall within the scope of the present application, and the patent protection scope of the present application should be subject to the claims.

What is claimed is:

1. A method for determining input information, wherein the method comprises:

in response to an action part of a body of a user executing an action, acquiring target Doppler measurement information about the action part or an acquisition part that corresponds to the action part, the target Doppler measurement information is blood-flow information;

determining target-velocity-related information corresponding to the target Doppler measurement information;

determining the action part and/or the action according to the target-velocity-related information and reference information; and determining input information according to the action part and/or the action.

2. The method of claim 1, wherein the determining the action part and/or the action according to the target-velocity-related information and the reference information comprises:

determining target difference information according to the target-velocity-related information and the reference information; and determining the action part and/or the action at least according to the target difference information.

3. The method of claim 2, wherein the determining target difference information according to the target-velocity-related information and the reference information comprises:

dividing the target-velocity-related information into multiple pieces of sub-target-velocity-related information according to a cycle; and respectively performing a cross-correlation calculation on the multiple pieces of sub-target-velocity-related information and the reference information, and determining the target difference information according to a calculation result.

4. The method of claim 2, wherein the reference information is reference-velocity-related information corresponding to reference Doppler measurement information acquired, in a case in which the action part does not execute the action, from an acquisition part of the target Doppler measurement information.

5. The method of claim 2, wherein the determining target difference information according to the target-velocity-related information and the reference information comprises:
comparing an amplitude value that is in the target-velocity-related information and a value of the reference information, and determining the target difference information according to a comparison result.

6. The method of claim 5, wherein the reference information is a first threshold.

7. The method of claim 2, wherein the determining the action part and/or the action at least according to the target difference information comprises:
respectively calculating the similarity between a waveform of the target difference information and at least one known waveform, and determining a target known waveform according to a calculation result; and
determining the action part and/or the action according to the target known waveform.

8. The method of claim 2, wherein the determining the action part and/or the action at least according to the target difference information comprises:
determining the action according to the number of wave troughs or wave crests comprised in the target difference information.

9. The method of claim 2, wherein the determining the action part and/or the action at least according to the target difference information comprises:
determining the action according to a cycle corresponding to the target difference information.

10. The method of claim 1, wherein the target-velocity-related information comprises target-blood-flow-speed information or target-blood-flow-flux information.

11. The method of claim 1, wherein the determining input information according to the action part and/or the action comprises:
determining a signal feature of the target Doppler measurement information; and
determining the input information according to the signal feature and the reference information.

12. The method of claim 1, wherein the action part is a hand or a wrist of the user.

13. A device for determining input information, wherein the device comprises:
an acquiring module, configured to acquire target Doppler measurement information about an action part of a body of a user or an acquisition part that corresponds to the action part, in response to the action part executing an action, the target Doppler measurement information is blood-flow information; and
a determining module, configured to
determine target-velocity-related information corresponding to the target Doppler measurement information;
determine the action part and/or the action according to the target-velocity-related information and reference information; and
determine input information according to the action part and/or the action.

14. The device of claim 13, wherein the determining module comprises:
a first determining subunit, configured to determine target difference information according to the target-velocity-related information and the reference information; and a second determining subunit, configured to determine the action part and/or the action at least according to the target difference information.

15. The device of claim 14, wherein the first determining subunit comprises:
a first-second-level subunit, configured to divide the target-velocity-related information into multiple pieces of sub-target-velocity-related information according to a cycle; and
a second-second-level subunit, configured to respectively perform a cross-correlation calculation on the multiple pieces of sub-target-velocity-related information and the reference information, and determine the target difference information according to a calculation result.

16. The device according to claim 14, wherein the first determining subunit is configured to compare an amplitude value that is the target-velocity-related information and a value of the reference information, and determine the target difference information according to a comparison result.

17. The device according to claim 14, wherein the second determining subunit comprises:
a third-second-level subunit, configured to respectively calculate the similarity between a waveform of the target difference information and at least one known waveform, and determine a target known waveform according to a calculation result; and
a fourth-second-level subunit, configured to determine the action part and/or the action according to the target known waveform.

18. The device of claim 14, wherein the second determining subunit is configured to determine the action according to the number of wave troughs or wave crests comprised in the target difference information.

19. The device of claim 14, wherein the second determining subunit is configured to determine the action according to a cycle corresponding to the target difference information.

20. The device of claim 13, wherein the determining module comprises:
a first determining submodule, configured to determine a signal feature of the target Doppler measurement information; and
a second determining submodule, configured to determine the input information according to the signal feature and the reference information.

21. A method for determining input information, wherein the method comprises:
in response to an action part of a body of a user executing an action, acquiring target blood-flow information about the action part or an acquisition part that corresponds to the action part;
determining target-velocity-related information corresponding to the target Doppler measurement information;
determining the action part and/or the action according to the target-velocity-related information and reference information; and
determining input information according to the action part and/or the action.

22. A device for determining input information, wherein the device comprises:
an acquiring module, configured to acquire target blood-flow information about an action part of a body of a user or an acquisition part that corresponds to the action part, in response to the action part of a body of a user executing an action; and a determining module, configured to
- determine target-velocity-related information corresponding to the target Doppler measurement information;
- determine the action part and/or the action according to the target-velocity-related information and reference information; and
- determine input information according to the action part and/or the action.

23. A wearable device, wherein the wearable device comprises a device for determining input information, the device for determining input information comprises:
- an acquiring module, configured to acquire target Doppler measurement information about an action part of a body of a user or an acquisition part that corresponds to the action part, in response to the action part executing an action, the target Doppler measurement information is blood-flow information; and
- a determining module, configured to
  - determine target-velocity-related information corresponding to the target Doppler measurement information;
  - determine the action part and/or the action according to the target-velocity-related information and reference information; and
  - determine input information according to the action part and/or the action.

* * * * *